US006573081B2

(12) United States Patent
Bernhardt et al.

(10) Patent No.: US 6,573,081 B2
(45) Date of Patent: Jun. 3, 2003

(54) METHOD FOR GROWING CIRCOVIRUSES

(75) Inventors: Dieter Bernhardt, Coelbe (DE); Thomas Weimer, Gladenbach (DE); Albrecht Groener, Marburg (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/947,551

(22) Filed: Sep. 7, 2001

(65) Prior Publication Data

US 2002/0055189 A1 May 9, 2002

(30) Foreign Application Priority Data

Sep. 8, 2000 (DE) ........................................ 100 44 648

(51) Int. Cl.[7] .............................. C12N 7/00; C12N 7/02

(52) U.S. Cl. .................. 435/235.1; 435/70.1; 435/70.3; 435/239

(58) Field of Search .......................... 435/5, 70.1, 70.3, 435/71.1, 173.9, 235.1, 239

(56) References Cited

U.S. PATENT DOCUMENTS

| | | | | |
|---|---|---|---|---|
| 4,500,513 A | * | 2/1985 | Brown et al. | 424/89 |
| 5,830,638 A | * | 11/1998 | Bernhardt et al. | 435/5 |
| 6,217,883 B1 | * | 4/2001 | Allan et al. | 424/202.1 |

OTHER PUBLICATIONS

Allan, G.M. et al. (1998) "Isolation of porcine circoviruslike viruses from pigs with a wasting disease in the USA and Europe" J. Vet. Diagn. Invest., vol. 10, pp. 3–10.

Clark, E.G., (1997) "Post–weaning miltisystemic wasting syndrome" Amer. Assn. Swine Practitioners Annual Meeting, pp. 499–501.

Springfield, C. et al. (2000) "TT Virus as human pathogen: significance and problems" Virus Genes, vol. 20, No. 1, pp. 35–45.

Derwent Abstract of FR 2 769 322 A1 (1999).

International Search Report, dated Dec. 13, 2001.

Handa, A. et al., "Prevalence of the newly described human circovirus, TTV, in United States blood donors," Transfusion, vol. 40, pp. 245–251 (2000).

Tischer, I. et al., "Presence of antibodies reacting with porcine circovirus in sera of humans, mice, and cattle, " Arch. Virol., vol. 140: pp. 1427–1439 (1995).

Morovzov, I. et al., "Detection of a novel strain of porcine circovirus in pigs with postweaning multisystemic wasting syndrom," J. Clin. Microbiol., vol. 36, No. 9, pp. 2535–2541 (1998).

Allan, J., "Nonhuman primates as organ donors?," Bull. WHO, vol. 77, No. 1, pp. 62–63 (1999).

Mankertz, A. et al., "Mapping and characterization of the origin of DNA replication of porcine circovirus," J. Virol., vol. 71, No. 3, pp. 2562–2566 (1997).

* cited by examiner

*Primary Examiner*—Hankyel T. Park
*Assistant Examiner*—Stacy S. Brown
(74) *Attorney, Agent, or Firm*—Finnegan, Henderson, Farabow, Garrett & Dunner, LLP

(57) ABSTRACT

Methods for growing circoviruses, in particular porcine circoviruses, which are obtained from an infected cell culture after one or more passages in cultures of porcine, bovine or human cells are described. When the porcine circoviruses grow, a cytopathogenic effect occurs in the cell culture.

3 Claims, No Drawings

METHOD FOR GROWING CIRCOVIRUSES

The invention relates to methods for growing and quantifying the infectious or antigenic amount and determining antibodies against circoviruses, in particular porcine circoviruses (PCV). The invention also relates to methods for detecting the reduction in circoviruses and circovirus-like viruses of humans through the method for manufacturing pharmaceuticals from biological material (1).

Porcine circoviruses are isometric non-enveloped viruses about 17 nm in size and having single-stranded circular DNA of 1.76 kb. Antibodies against porcine circovirus have been found in serum from humans, mice and cattle by means of an indirect immunofluorescence detection (IFA) and by means of the ELISA method (2). Antibodies are detected in 53 to 92% of slaughter pigs (3). The clinical significance of PCV is still unknown. A new type or porcine circovirus, which leads to lesions in pig tissues and can be correlated with disease symptoms, has recently been detected. This so-called type 2 (PCV2) differs from the aforementioned type 1 (PCV1) mainly in terms of the pathogenicity (3 and 4).

Although porcine circovirus can be detected as contaminating agent in pig tissue cultures, it has not to date been possible to grow the virus in vitro and establish a routine test for growth and for quantitative detection of the virus, e.g. on the basis of a cytopathogenic effect (CPE), in the virus-replicating cells (2).

However, PCV is detected in vivo by means of the polymerase chain reaction in lymph nodes and cells of the spleen, tonsils, liver, heart, lungs, nasal mucosa, kidneys, pancreas and intestine (3). Since pig organs are used for human transplantation (5), porcine circovirus should be regarded as a potential risk virus for humans.

The object of the present invention was therefore to develop a method for cultivating porcine circovirus in vitro in order to be able to examine its infectivity. It was additionally intended to develop a method for neutralizing porcine circovirus by specific antibodies and removing it from biological materials from pigs, humans or other vertebrates, so that these materials can be employed without reservations directly or indirectly for therapeutic purposes, e.g. for obtaining insulin, heparin, blood and plasma, cell culture media and constituents thereof, including trypsin, and for cells for producing recombinant proteins. It was finally intended that successful growing of PCV in cell cultures would also make it possible to produce a vaccine by methods known per se. This may involve using inactivated PCT or an avirulent PCV strain (e.g. through selection of an avirulent PCV strain after adaptation to various cell cultures and/or after treatment of infected cell cultures with mutagens or after genetic modification of the PCV) as live vaccine. In addition, the antigenic material obtained from grown porcine circoviruses can also be employed for diagnostic purposes.

This object is achieved by a method for growing circoviruses, in particular porcine circoviruses (PCV), in which circoviruses obtained from an infected cell culture grow in cultures of porcine, bovine or human cells after one or more passages in the cell cultures.

For the method of the invention, porcine circoviruses obtained from a PK15 (=porcine kidney) cell culture inapparently infected with PCV were, after passage in other cell cultures, in particular porcine cell cultures, grown in these cell cultures, with a cytopathogenic effect being displayed. The presence of porcine circoviruses was in this case verified with the aid of a specific nested polymerase chain reaction (PCR). Primers with the following DNA sequences were employed for this:

1. PCR plus: GAG AGG AAG GTT TGG AAG AGG (946–966) (SEQ ID NO. 1)
1. PCR minus: CCA CTG GCT CTT CCC ACA ACC (1358–1338) (SEQ ID NO. 2).
2. PCR plus: GGT GAA GTG GTA TTT TGG TGC C (1025–1046) (SEQ ID NO. 3)
2. PCR minus: CTA TGA CGT GTA CAG CTG TCT TCC (1326–1303) (SEQ ID NO. 4)

These primers were selected from the origin of replication (7).

When carrying out the method of the invention, it was observed that the porcine circoviruses cannot be grown equally well in all cultures of various mammalian and human cells. Growth was successful in cultures of cells from various porcine organs, from bovine kidney, bovine lung and human lung. A cell culture which is very suitable for successful growth of porcine circovirus and which was developed from fetal porcine testis was deposited on Jul. 10, 2000, under the provisions of the Budapest Treaty at Deutsche Sammiung Von Mikroorganismen und Zelikulturen GmbH (DSMZ), Mascheroder Weg 1b, D—38124 Braunschweig, German, and was assigned Accession No. FSHO-DSM ACC 2466.

The ELISA method is very suitable for quantitative detection of antibodies present in serum against porcine circovirus. This entails circoviruses being incubated, after adsorption onto a support material, with the serum to be investigated and thus being bound to a primary antibody present in the serum. A secondary labeled antibody directed against the primary antibody is then brought into contact therewith and, after the unbound secondary antibody has been washed out, the light signal emitted by the bound labeled antibody (extinction) is measured. The sandwich method known to the skilled worker is suitable for detecting the circovirus antigen, in which case an antibody against circoviruses which is bound to a support material binds the antigen in the serum to be investigated; a (labeled) antibody directed against circovirus antigen is then brought into contact therewith and, after the unbound antibody has been washed out, the light signal emitted by the bound labeled antibody (extinction) is measured.

Sera containing neutralizing antibodies against porcine circovirus are suitable for neutralizing circoviruses in biological material. Neutralizing antibodies have been found in porcine sera and human immunoglobulin (γ-globulin). A human immunoglobulin particularly suitable for neutralizing circoviruses in biological material is one obtained from high-titer human donors who have a titer of specific antibodies which is at least two to three times higher than normal donors, the average PCV antibody titer being determined on a plasma pool from at least 1000 donors.

The virus safety of pharmaceuticals of biological origin (e.g. from human blood/plasma, from cell cultures, from animal organs/tissues) is investigated as required by the authorities (e.g. CPMP/BWP/268/95: Note for guidance on virus validation studies: the design, contribution and interpretation of studies validating the inactivation and removal of viruses; CPMP/BWP/269/95 rev. 3: Note for guidance on plasma-derived medicinal products); in these so-called virus validation studies, viruses are deliberately added to material at various production steps in the method of manufacture of biologicals, and the removal and/or inactivation of the viruses by the step in the method is determined. The viruses used for this investigation either should possibly occur in the biological starting material or, if these viruses cannot be grown in vitro, are model viruses with physico-chemical properties as similar as possible to the contaminating viruses. An example of a model virus for the human circovirus TTV is PCV. In investigations of a step in the method of manufacture of therapeutic compositions from biological material—heat treatment at 60° C. in stabilized aqueous solution—it emerged that the porcine circovirus is labile and could be inactivated within a few hours; it is thus possible to demonstrate the capacity of the method of manufacturing biologicals to inactivate TTV by a heat treatment. It is possible analogously to investigate other steps in the manufacturing process for the ability to remove TTV (e.g. by precipitation, adsorption or chromatography or filtration steps) or inactivate TTV (e.g. by chaotropic salts or substances which intercalate in nucleic acids, or by irradiation with high-energy rays) using PCV. It is additionally possible to establish the capacity for inactivating and/or removing viruses also, for example, for additives in the production of pharmaceuticals, such as, for example, sera and other ingredients of media for cell cultures for producing recombinant proteins or monoclonal antibodies for affinity chromatography for purifying and concentrating active ingredients.

The invention is explained in detail by the following examples:

EXAMPLE 1

The culture supernatant from a PK15 culture which had been maintained for many tissue passages and which showed, five days after passaging, a positive signal for PCV in the PCR was subcultured in the ratio 1:100 on cell cultures of various cell lines which had been freshly seeded out in T25 cell culture bottles.

The following permanent cultures of porcine cells were inoculated:

| | |
|---|---|
| Fetal porcine kidney | FPK |
| Fetal porcine thyroid | FPTh |
| Fetal porcine testis | FPTe |
| Fetal porcine spleen | FPSp |
| Fetal porcine heart | FPH |
| Fetal porcine skin | FPSk |
| Porcine kidney | PS |

Ten days after inoculation, all the cultures apart from FPTh and FPSk showed cytopathogenic changes (CPE). The cell culture supernatant was harvested from the CPE-positive cultures and stored at −80° C. until used for further experiments.

A second passage of the CPE-causing agent was carried out on the homologous cell cultures by inoculating these cell cultures with the cell culture supernatant from the first passage.

A distinct CPE was evident after only four days in the PS cells; with the other cultures, the CPE was visible for the first time six days after inoculation. Using a specific PCR employing the abovementioned primers it was possible to detect PCV in the PS cell culture showing a CPE, while no PCR signal was evident in the corresponding control cells without inoculation of the PK15 cell culture supernatant.

EXAMPLE 2

The PCV grown in the PS cell culture was quantified in the harvested cell culture supernatant which had been centrifuged at low speed, by means of the end-point dilution method. The cell culture supernatant was diluted in 10-fold dilution steps and transferred to PS cell cultures in microtiter plates, and the PCV growth was evaluated as cytopathogenic effect (CPE). Final reading of the test took place seven days after the infection, and the virus titer ($CCID_{50}$—cell culture infective dose 50%—in logio) was calculated by methods known to the skilled worker (6). Since circoviruses are non-enveloped viruses, as a check and to confirm that the cytopathogenic effect is attributable to the growth of PCV in the cell culture, part of the PS cell culture supernatant was treated with chloroform; this method is known to the skilled worker to inactivate enveloped viruses. Comparative titration of the untreated and chloroform-treated virus suspension in PS cells revealed no difference in titer (Table 1). This result, together with the specific PCR result, confirms growth of PCV in the cell culture, in particular in porcine cells.

TABLE 1

Quantitative determination of PCV grown in PS cells

| Virus suspension | $\log_{10} CCID50/ml$ |
|---|---|
| PS cell culture supernatant | 7.8 |
| PS cell culture supernatant, chloroform-treated | 7.6

TABLE 2-continued

Demonstration of the growth of PCV in
cultures of various mammalian and human cells

|  | 1st passage* | 2nd passage* | 3rd passage* |
|---|---|---|---|
| FRhK 4 = Fetal Rhesus Kidney | — | — | — |
| PH-2 = Fetal Cynomolgus Kidney | — | — | — |
| A549 = Human Lung | — | — | — |
| Ma23 = Human Lung | — | — | — |
| Mabt = Human Lung | ? | + | + |

*Appearance of the CPE
—no CPE
? CPE doubtful/not pronounced
+ CPE pronounced

EXAMPLE 4

After in vitro growth of PCV in cell cultures had succeeded, the capacity of sera from various mammals to neutralize PCV was investigated. These investigations indicate in which mammals PCV grows, with subsequent seroconversion, or whether their sera contain antibodies which cross-react with PCV. However, it was not possible with the present experimental design to distinguish reliably between these two possibilities. Various sera from individual animals (dog, cat, horse, pig, monkey) and pooled sera from several animals (cattle) or immunoglobulin concentrates from human pooled plasma were tested in the neutralization test—antibody dilution and constant amount of virus (about 100 $CCID_{50}$). As Table 3 below shows, neutralizing antibodies against porcine circovirus are detectable only in porcine sera and human immunoglobulin (e.g. Beriglobin 7).

TABLE 3

Detection of PCV-neutralizing antibodies in
sera from various species

| Species | Number of sera investigated | Number of PCV-positive sera |
|---|---|---|
| Beriglobin* batches | 24 | 24 |
| Dog | 10 | 0 |
| Cat | 10 | 0 |
| Horse | 10 | 0 |
| Bovine | 10 | 0 |
| Pig | 10 | 10 |
| Monkey | 10 | 0 |

*purified human gamma-globulin concentrate from donated pool
NT index > 0.5 was assessed as positive

EXAMPLE 5

The PCV-neutralizing and non-neutralizing antibodies can also be detected with other in vitro methods known to the skilled worker, e.g. with enzyme immunoassays (EIA). Adsorption of PCV onto a solid phase (e.g. polystyrene, nylon or cellulose) with subsequent incubation of the sera to be investigated and further incubation with enzyme-labeled, secondary antibodies directed against the primary antibodies present in the sera leads to quantification of antibodies directed against PCV in the serum to be investigated.

PCV-containing cell culture supernatant from PS cells was prediluted 1:100 in 0.1 M NaOH and pipetted in a geometric dilution series into an ELISA microtiter plate (dilution buffer 0.05 M $Na_2CO_3$, pH 9.6). The color intensity was measured by methods known to the skilled worker for blocking the plate, and incubating with serum to be investigated and labeled antibodies directed against the serum to be investigated (Table 4). The example shows that antibodies against porcine circovirus are detectable only in porcine sera and human immunoglobulin concentrates.

TABLE 4

ELISA of various sera for detecting
antibodies against porcine circoviruses
(extinction)

| Virus dilution | Human immunoglobulin concentrate (Beriglobin P) | Porcine serum | Equine serum |
|---|---|---|---|
| 1:200 | >2.000 | >2.000 | 0.386 |
| 1:400 | 1.983 | >2.000 | 0.426 |
| 1:800 | 1.168 | 1.852 | 0.189 |
| 1:1600 | 0.726 | 1.233 | 0.253 |
| 1:3200 | 0.268 | 0.706 | 0.335 |
| 1:6400 | 0.381 | 0.457 | 0.129 |

EXAMPLE 6

In the manufacture of therapeutic compositions or substances intended to be employed for their manufacture from biological material it is necessary to inactivate or remove viruses which are potentially present. For this reason, the thermal stability of porcine circovirus was tested in various media in a further series of tests at 60° C. (pasteurization in aqueous solution):

a) in Eagle's minimal essential medium (EME medium)

b) in 5% strength human serum albumin solution (HSA)

c) in pasteurization buffer for blood coagulation (FVIII) products (aqueous solution stabilized with sucrose and glycine).

For this purpose, PCV was produced as in Example 2, added (spiked) 1:11 v/v to the three media mentioned above and heated in a water bath at 60° C. After the stated times, samples were taken for titration of the remaining virus and titrated on PS cells.

Final reading of the titer took place 7 days after setting up the test by observing the cytopathogenic effect under the microscope; the results are shown in Table 5.

As the results show, PCV is unstable to physico-chemical parameters such as elevated temperature. Stabilizers added to the pasteurization buffer for factor VIII products in order to stabilize this factor during the pasteurization (heat treatment at 600° C. in stabilized aqueous solution) likewise stabilize PCV to a certain extent. It is thus possible to use circoviruses for investigating the capacity of a method of manufacture or of a diagnostic aid to inactivate and/or remove circoviruses or related viruses.

TABLE 5

| | Virus titer ($\log_{10}$ CCID$_{50}$/ml) after incubation of PCV in various media at 60° C. | | |
|---|---|---|---|
| Pasteurization time [h] | PCV in cell culture medium | PCV in 5% human serum albumin | PCV in factor VIII pasteurization buffer |
| 0 | 5.9 | 5.8 | 5.8 |
| 1 | ≦1.5 | 1.8 | 4.9 |
| 2 | ≦1.5 | ≦1.5 | 3.5 |
| 4 | ≦1.5 | ≦1.5 | 2.9 |
| 6 | ≦1.5 | ≦1.5 | 1.8 |
| 8 | ≦1.5 | ≦1.5 | ≦1.5 |

COMPILATION OF LITERATURE

1. Handa, A. et al., Prevalence of the newly described human circovirus, TTV, in United States blood donors.—Transfusion 40, 245–251 (2000)
2. Tischer, I., Bode, L., Apodaca, J., Timm, H., Peters, D., Rasch, R., Pociuli, S. and Gerike, E. "Presence of antibodies reacting with Porcine Circovirus in sera of humans, mice and cattle"; Arch. Virol. 140, 1427–1439 (1995)
3. Morovsov,, I., Sirinarumitr, T., Sorden, S. D., Halbur, P. G., Morgan, M. K., Yoon, K.-I. and Paul, P. S. "Detection of a novel strain of Porcine Circovirus in pigs with postweaning multisystemic wasting syndrome" J. Clin. Microbiol. 36, 2535–2541 (1998)
4. Hinrichs, U. et al., Erster Nachweis einer Infektion mit dem porzinen Circovirus Typ 2 in Deutschland.—Tierärztliche Umschau 54, 255–258 (1999)
5. Allan, J. S. "Nonhuman primates as organ donors?" Bull. WHO 77 (1), 62–63 (1999)
6. Kärber, C. "Beitrag zur kollektiven Behandlung pharmakologischer Reihenversuche" Arch. Exp. Path. Pharmak. 162:480–487 (1931)
7. Mankertz, A. et al., 1997. Mapping and characterization of the origin of DNA replication of porcine circovirus. J. Gen. Virol. 71:2562–2566.

What is claimed is:

1. A method for growing circoviruses, which comprises the steps of
   a) obtaining circoviruses from an infected first cell culture,
   b) inoculating a second cell culture with the circoviruses,
   c) making one or more passages of the second cell culture,
   d) analyzing said second cell culture for a cytopathogenic effect (CPE), and
   e) harvesting the circoviruses from the CPE positive cultures.

2. The method as claimed in claim 1, wherein the circoviruses are porcine circoviruses.

3. The method as claimed in claim 1, wherein the second cell culture comprises cells of porcine, bovine or human origin.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
gagaggaagg tttggaagag g                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
ccactggctc ttcccacaac c                                          21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 3
ggtgaagtgg tattttggtg cc                                         22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
```

-continued

```
ctatgacgtg tacagctgtc ttcc                    24
```